United States Patent
Char et al.

(10) Patent No.: US 8,349,453 B2
(45) Date of Patent: Jan. 8, 2013

(54) METAL ION SENSOR AND FABRICATING METHOD THEREOF

(75) Inventors: Kookheon Char, Soecho-gu (KR); Hosub Kim, Geumcheon-gu (KR)

(73) Assignee: SNU R&DB Foundation, Seoul (KR)

( * ) Notice: Subject to any disclaimer, the term of this patent is extended or adjusted under 35 U.S.C. 154(b) by 628 days.

(21) Appl. No.: 12/592,647

(22) Filed: Dec. 1, 2009

(65) Prior Publication Data

US 2010/0252807 A1 Oct. 7, 2010

(30) Foreign Application Priority Data

Apr. 3, 2009 (KR) .................. 10-2009-0028820

(51) Int. Cl.
*B32B 5/16* (2006.01)
(52) U.S. Cl. ........ 428/403; 428/404; 428/406; 428/407; 427/212; 977/831; 977/834; 977/953
(58) Field of Classification Search .................. 428/403, 428/404, 406, 407; 427/212; 977/831, 834, 977/953
See application file for complete search history.

(56) References Cited

U.S. PATENT DOCUMENTS

| 7,371,457 B2 * | 5/2008 | Oldenburg et al. ........... 428/403 |
| 7,713,624 B2 * | 5/2010 | Meyer et al. .................. 428/403 |
| 7,807,265 B2 * | 10/2010 | Santra et al. .................. 428/403 |
| 8,221,651 B2 * | 7/2012 | Murase et al. ......... 252/301.4 R |
| 8,287,761 B2 * | 10/2012 | Schrier et al. ........... 252/301.6 S |

* cited by examiner

*Primary Examiner* — Leszek Kiliman
(74) *Attorney, Agent, or Firm* — Sherr & Jiang, PLLC

(57) ABSTRACT

A metal ion sensor is provided. The metal ion sensor includes a nanoparticle core doped with a first luminescent material and a shell enclosing the nanoparticle core. The shell includes a second luminescent material and binding sites of outer metal ions. The first luminescent material and the second luminescent material emit light with mutually different colors when excited by an excitation source. The luminescence intensity of the light emitted from the second luminescent material varies in accordance with the binding amount of the outer metal ions, such that the emission color of the combined luminescence of the first luminescent material and the second luminescent material is changed.

19 Claims, 9 Drawing Sheets

FIG. 1
(a)
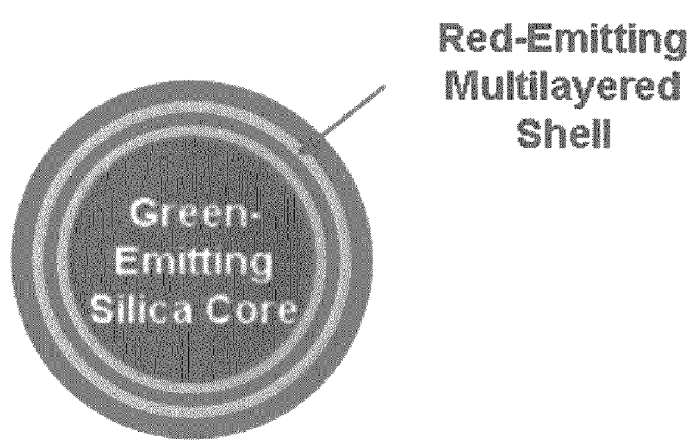
Cross-Sectional View
(b)
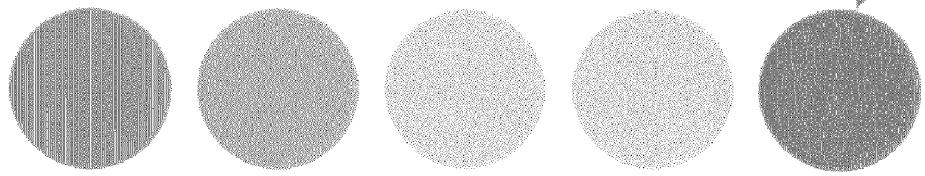
Color Changes w/ Cu(II) Ions FIG 3
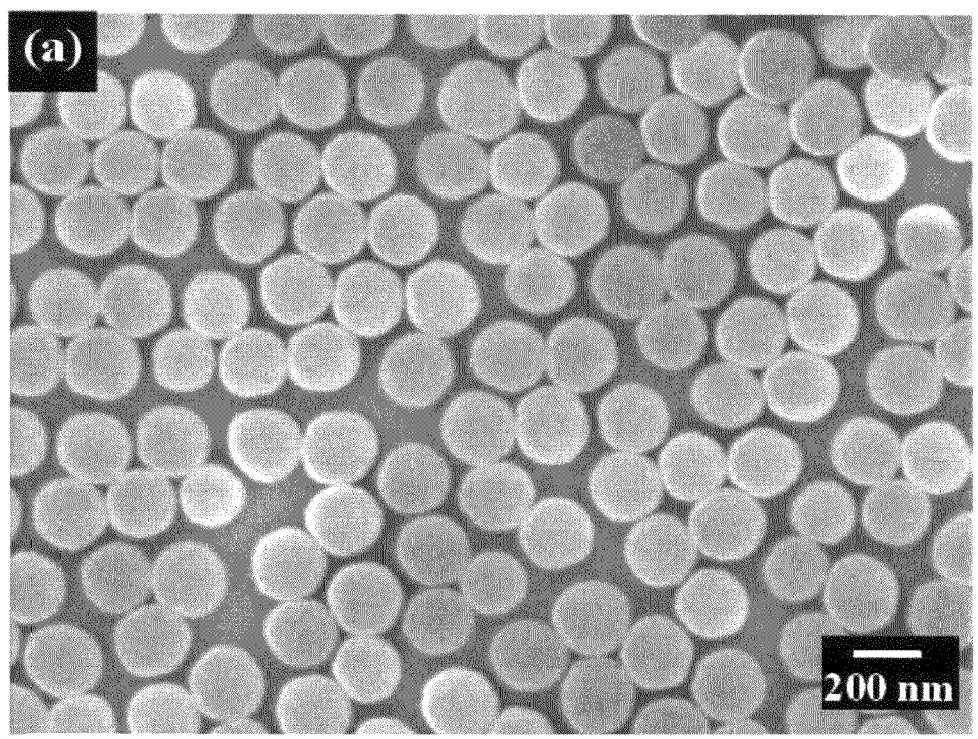
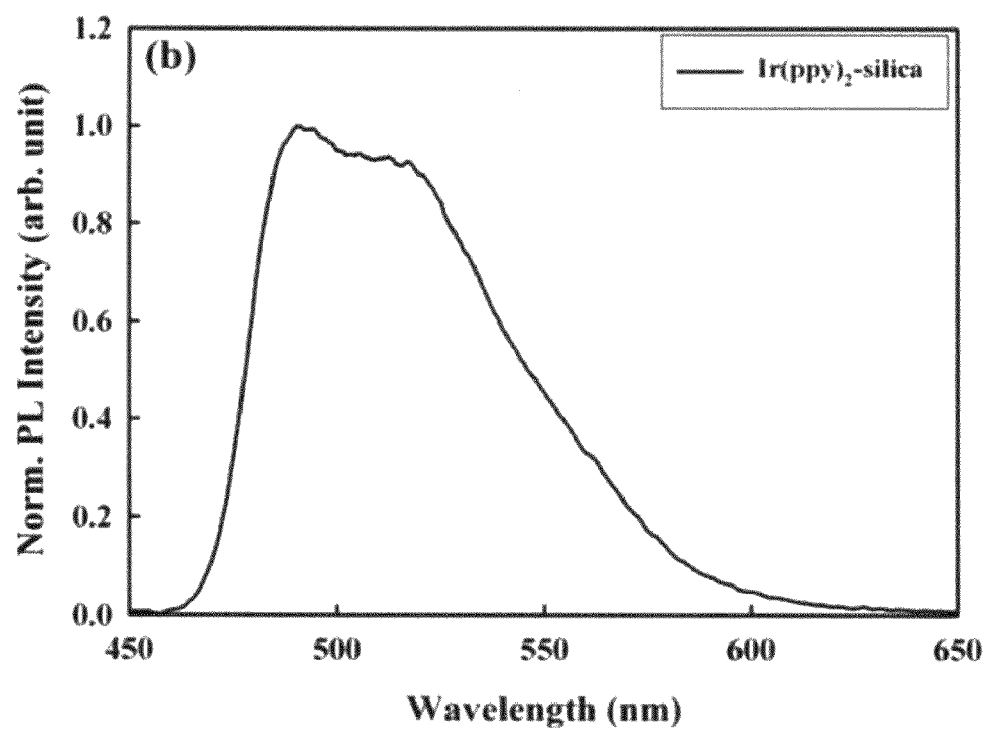

FIG 8
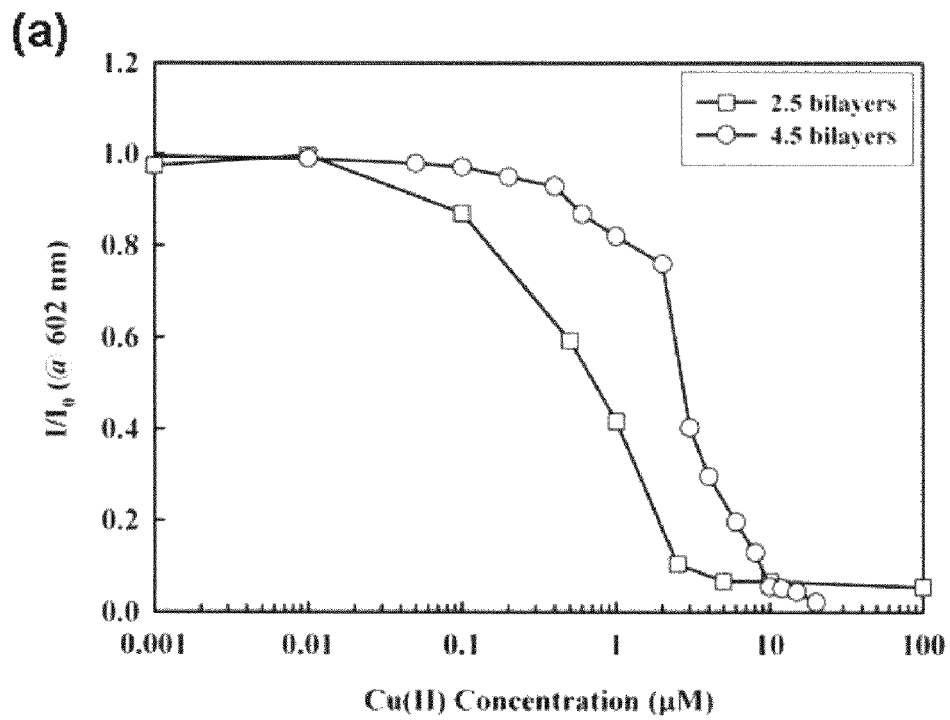
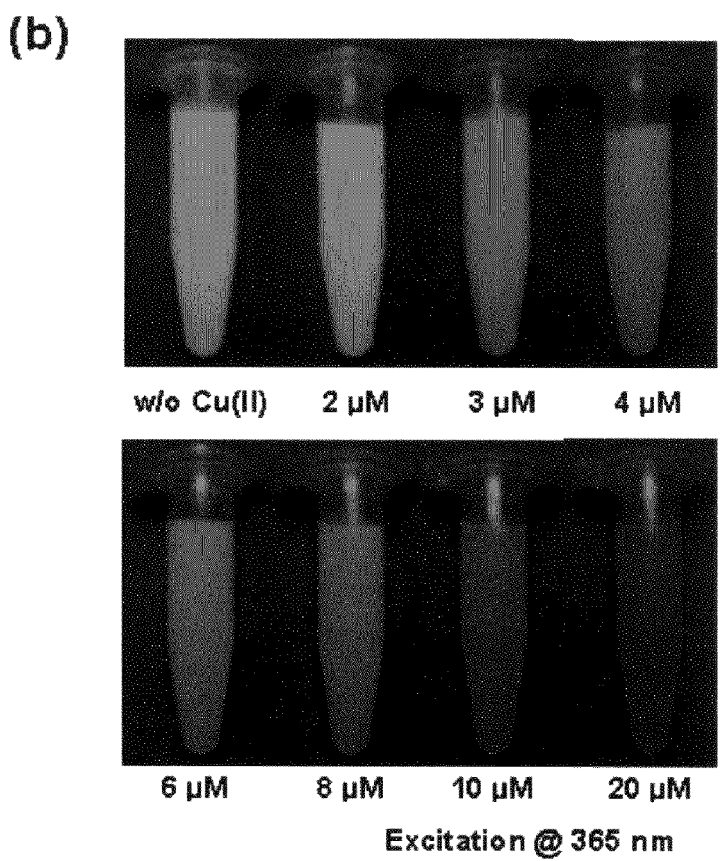

METAL ION SENSOR AND FABRICATING METHOD THEREOF

CROSS REFERENCE TO PRIOR APPLICATIONS

This application claims priority to Korean Patent Application No. 10-2009-0028820 (filed on Apr. 3, 2009) which is hereby incorporated by reference in its entirety.

TECHNICAL FIELD

The described technology relates to a metal ion sensor adapted to rapidly and quantitatively measure the concentration of a metal ion in an aqueous solution with high selectivity.

BACKGROUND

Copper is widely used for many industrial applications because of the excellent processing characteristic and high thermal and electric conductivity thereof. Copper ion is one of the essential elements for various living organisms. However, the concentration of the copper ion increases through the industrial utilization, causing serious toxicity to the living organisms. Moreover, when other heavy metals such as cadmium and mercury are absorbed in body systems, itai-itai disease and Minamata disease may be generated, respectively. Accordingly, many researchers have been studied on the fabrication of metal ion sensors for the easy detection of heavy metals. However, the conventional metal ion sensors are operated in non-pure water i.e. in organic solvent or mixed solution of water and organic solvent due to the solubility of the sensing materials. Furthermore, the quantitatively analysis of metal ions can be hardly occurred without using spectroscopic equipments and the detecting speed of the sensor is slow, resulting in a limitation to practical applications thereof.

SUMMARY

In accordance with some embodiments, a metal ion sensor is provided. The metal ion sensor includes a nanoparticle core doped with a first luminescent material and a shell enclosing the nanoparticle core. The shell includes a second luminescent material and binding sites of outer metal ions. The first luminescent material and the second luminescent material emit light with mutually different colors when excited by an excitation source. The luminescence intensity of the light emitted from the second luminescent material varies in accordance with the binding amount of the outer metal ions, such that the emission color of the combined luminescence of the first luminescent material and the second luminescent material is changed.

In one embodiment, the shell may include a multilayered shell.

In another embodiment, the shell may include polymeric bilayers. The polymeric bilayer may be formed by noncovalent interaction or covalent interaction between each polymer layer composing the polymeric bilayer. The noncovalent interaction may include hydrogen bonding, charge-charge interaction, dipole interaction, etc. A detection concentration range of the outer metal ions may be modulated by changing the bilayer number in the multilayered shell.

In still another embodiment, the shell may include an alternate stacking structure of a first polyelectrolyte layer and a second polyelectrolyte layer, the first polyelectrolyte layer and the second polyelectrolyte layer may have opposite electric charges to each other. The first polyelectrolyte or the second polyelectrolyte may be grafted with a host material to improve the luminescence intensity of the first luminescent material or the second luminescent material.

In still another embodiment, the nanoparticle core may be selected from silica beads, quantum dots, inorganic nanoparticles, or polymer beads.

In still another embodiment, the first luminescent material and/or the second luminescent material may be selected from dyes, pigments, or semiconductor nanoparticles.

In still another embodiment, the binding sites may include nonionic functional groups or negatively charged functional groups.

In accordance with some embodiments, a solid-state metal ion sensor fabricated by applying a metal ion sensor to a substrate is provided. The metal ion sensor includes a nanoparticle core doped with a first luminescent material, and a multilayered shell enclosing the nanoparticle core. The multilayered shell comprises a second luminescent material and binding sites of outer metal ions. The first luminescent material and the second luminescent material emit light with mutually different colors when excited by an excitation source. The luminescence intensity of the light emitted from the second luminescent material varies in accordance with the binding amount of the outer metal ions, such that the emission color of the combined luminescence of the first luminescent material and the second luminescent material is changed.

In one embodiment, the multilayered shell may include polymeric bilayers.

In another embodiment, the multilayered shell may include an alternate stacking structure of a first polyelectrolyte layer and a second polyelectrolyte layer, the first polyelectrolyte layer and the second polyelectrolyte layer having opposite electric charges to each other.

In accordance with some embodiments, a copper ion sensor is provided. The copper ion sensor includes a nanoparticle core and a multilayered shell, which encloses the nanoparticle core. The nanoparticle core is doped with a first luminescent material. The multilayered shell is doped with a second luminescent material having a different luminescence color from that of the first luminescent material. The multilayered shell has an alternate stacking structure of a negatively charged polyelectrolyte layer and a positively charged polyelectrolyte layer. The multilayered shell has binding sites of outer copper ions. The luminescence from the multilayered shell is selectively quenched by the binding of copper ions when the first luminescent material and the second luminescent material are excited by an excitation source.

In one embodiment, the nanoparticle core may be selected from silica beads, quantum dots, inorganic nanoparticles, or polymer beads.

In another embodiment, the positively charged polyelectrolyte layer may include a polyelectrolyte in which the second luminescent material is grafted onto polyethylene imine (PEI).

In still another embodiment, the negatively charged polyelectrolyte layer may include poly(acrylic acid) grafted with CBZ (carbazole) or CBP (4,4'-N,N'-dicarbazole-biphenyl).

In still another embodiment, a detection concentration range of the outer copper ions is modulated by changing the bilayer number in the multilayered shell.

In accordance with some embodiments, a method of fabricating a metal ion sensor is provided. The method includes forming a nanoparticle core doped with a first luminescent material, providing a first polyelectrolyte that is doped with a second luminescent material and has binding sites of outer metal ions, providing a second polyelectrolyte that has an opposite electric charge to that of the first polyelectrolyte, and forming a multilayered shell by alternately depositing the first polyelectrolyte and the second polyelectrolyte on the nanoparticle core. The first luminescent material and the second luminescent material emit light with mutually different colors when excited by an excitation source. The luminescence intensity of the light emitted from the second luminescent material varies in accordance with the binding amount of the outer metal ions, such that the color of the combined luminescence of the first luminescent material and the second luminescent material is changed.

The Summary is provided to introduce a selection of concepts in a simplified form that are further described below in the Detailed Description. The Summary is not intended to identify key features or essential features of the claimed subject matter, nor is it intended to be used as an aid in determining the scope of the claimed subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For fuller understanding of the nature and objects of the present disclosure, reference should be made to the following detailed description taken in conjunction with the accompanying drawings in which:

FIG. 1 shows (a) a copper ion sensor as an example of a metal ion sensor and (b) a color variation of the copper ion sensor corresponding to the concentrations of copper ions;

FIG. 3 shows (a) an field emission scanning electron microscope (FE-SEM) image of a prepared $Ir(ppy)_2$-silica nanoparticles and (b) luminescence spectrum of the $Ir(ppy)_2$-silica nanoparticles;

FIG. 8 shows (a) a graph showing a ratio $(I/I_0)$ of the luminescence intensity (I) at 602 nm with the presence of Cu(II) ions to the luminescence intensity $(I_0)$ at 602 nm without Cu(II) ions for a copper sensor having a $Ir(ppy)_2$-silica/$(CBZ-PAA/Ir(piq)_2-PEI)_n$ core/shell structure and (b) photographs for depicting luminescence of a copper ion sensor having a $Ir(ppy)_2$-silica/$(CBZ-PAA/Ir(piq)_2-PEI)_{4.5}$ core/shell structure under UV irradiation of 365 nm with various Cu(II) ion concentrations.

DETAILED DESCRIPTION

Figure 2:
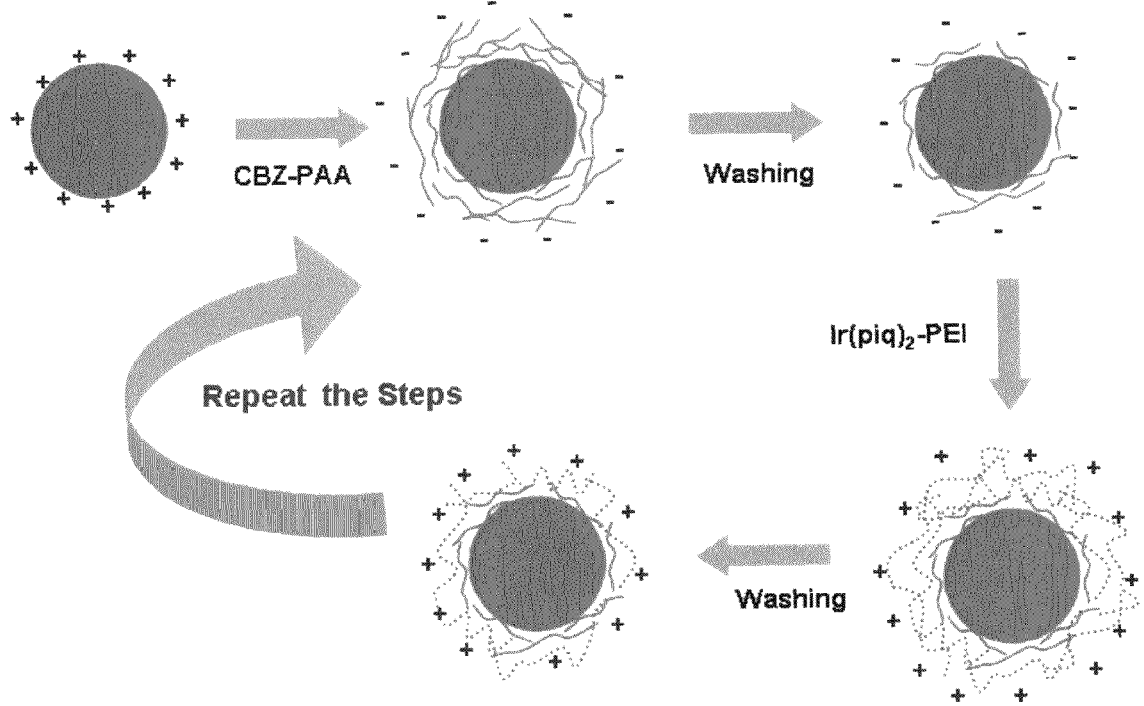
FIG. 2 is a schematical view depicting one embodiment of a process of forming a multilayered shell of a metal ion sensor using a layer-by-layer deposition method.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the components of the present disclosure, as generally described herein, and illustrated in the Figures, can be arranged, substituted, combined, and designed in a wide variety of different configurations, all of which are explicitly contemplated and make part of this disclosure. It will also be understood that when an element or layer is referred to as being "on" or "connected to" another element or layer, the element or layer may be directly on or connected to the other element or layer or intervening elements or layers may be present.

A metal ion sensor may include a core/shell-structured nanoparticle, more specifically, the metal ion sensor may include a nanoparticle core and a multilayered shell structure, which encloses the nanoparticle core. The nanoparticle core may be doped with a first luminescent material. The multilayered shell may surround the nanoparticle core and may include a first polyelectrolyte, which has a second luminescent material, and a second polyelectrolyte, which has an opposite electric charge to that of the first polyelectrolyte. The multilayered shell may have a stacking structure of two or more different polyelectrolyte layers.

The size of the metal ion sensor may be, for example, between several tens of nm and several tens of μm. The nanoparticle core may be selected from silica beads, quantum dots, inorganic nanoparticles, or polymer beads.

The first luminescent material may emit fluorescent or phosphorescent light by an excitation source. Examples of the excitation source may include ultraviolet rays, blue lights, electron beams etc. In one embodiment, the first luminescent material may be selected from, but is not limited hereto, dyes, pigments or semiconductor nanoparticles. In another embodiment, the first luminescent material may be a transition metal complex dye. In case that the first luminescent material is the transition metal complex, luminescence spectra of various wavelength ranges may be acquired corresponding to the kinds of ligands coordinated to the transition metal.

The first luminescent material may be doped with various manners into the nanoparticle core. Provided that the nanoparticle core consists of a silica bead, silanol groups may be attached to the transition metal complex by the ligand exchange reaction of the transition metal complex used as the first luminescent material and the transition metal complex with silanol groups may be bound to the silica precursor through the sol-gel process, thus the first luminescent material may be doped into the silica nanoparticle. Provided that the nanoparticle core consists of a polymer bead, dye molecules may be incorporated into the polymer bead through the swelling process.

The multilayered shell may include a polymeric bilayer formed by a layer-by-layer deposition. The layer-by-layer deposition may be implemented by alternately depositing at least two polymer layers. For example, the polymeric bilayer may be formed by alternately depositing a positively charged polymer layer and a negatively charged polymer layer. In one embodiment, the polymeric bilayer may be formed through noncovalent interaction (for example, hydrogen bonding, charge-charge interaction, dipole interaction, etc.) or covalent interaction between each polymer layer of composing the polymeric bilayer. The thickness of the shell is in proportion to the number of deposition cycles. One of the positively charged layer and the negatively charged layer may include the second luminescent material while the other may include a host material for increasing the luminescence intensity of the second luminescent material. The doping amount of the second luminescent material may increase corresponding to the increase of the thickness of the shell.

The multilayered shell is provided with polyelectrolytes so that the metal ion sensor in a nanoparticle form may be dispersed in water. The multilayered shell has the second luminescent material and binding sites for specific metal ions.

The second luminescent material may emit either fluorescent or phosphorescent light. In one embodiment, the second luminescent material may be selected from, but is not limited hereto, dyes, pigments or semiconductor nanoparticles. In another embodiment, the second luminescent material may be a transition metal complex dye. When the first luminescent material is the transition metal complex, luminescence spectra of various wavelength ranges may be acquired corresponding to the kinds of ligands coordinated to the transition metal.

In case that the second luminescent material is the transition metal complex, the second luminescent material may be grafted onto the polyelectrolyte based on the ligand exchange reaction. The binding sites at the multilayered shell may provide functional groups to interact with outer metal ions. The binding sites may include nonionic or ionic groups. Examples of the nonionic functional groups may be, but are not limited hereto, groups containing nitrogen such as amines and amides; or groups containing oxygen such as ketones and carboxylic acids. Since metal ions may be bound with ionic functional groups via the electrostatic attractive force, negatively charged functional groups may also be used as the binding sites. For example, negatively charged functional groups may include materials containing carboxylate groups or sulfonate groups.

The light emitted from the second luminescent material may have different color from that of the first luminescent material. When metal ions are bound with through the binding sites in the shell doped with the second luminescent material, excited electrons move towards metal ions, inducing the quenching of the luminescence. Thus, the luminescence intensity from the second luminescent material may be reduced in accordance with the binding amount of metal ions.

According to the aforesaid quenching behavior, the color of the combined luminescence of the first luminescent material and the second luminescent material may be changed. The color changes may be easily observed through the naked eyes, and thus quantitative analysis of metal ion concentration may be carried out within a short time.

FIG. 1 shows (a) a copper ion sensor as an example of a metal ion sensor and (b) a color variation of the copper ion sensor corresponding to the concentrations of copper ions.

The copper ion sensor shown in FIG. 1 as an example may be provided with a green luminescent nanoparticle core covered by a red luminescent multilayered shell. In such a core/shell structure, the quenching of red luminescence may lead a variation of relative intensity of red luminescence and green luminescence, and thus the color of luminescence combined by red and green may be changed. The changes in luminescence color proportional to the concentration of Cu(II) ions may be achieved by the selective quenching of red luminescent material presented in the multilayered shell. For the selective quenching, the green luminescent material may be protected from quenchers, Cu(II) ions, by the incorporation into the silica nanoparticle.

As an example of the green luminescent material, iridium complex having 2-phenylpyridine (ppy) ligands may be used. The silica nanoparticle embedded with Ir(III)-complex may be synthesized as follows by using the modified Stöber method. For the covalent immobilization of Ir(III)-complex inside the silica nanoparticle, silicon alkoxide group is introduced into Ir(III)-complex based on the simple ligand exchange reaction between cyclometalated Ir(III)-μ-chloro-bridged dimers having 2-phenylpyridine (ppy) ligands, [Ir(ppy)$_2$Cl]$_2$, and (3-aminopropyl)triethoxysilane (APTES) in tetrahydrofuran (THF). The amine groups of APTES are easily attached to iridium atoms by the facile cleavage of iridium-chlorine bonds, and Si(OC$_2$H$_5$)$_3$ groups are coupled with tetraethoxysilane (TEOS) precursor through the hydrolytic condensation during the sol-gel process. The below Formula 1 represents the aforementioned synthesis process.

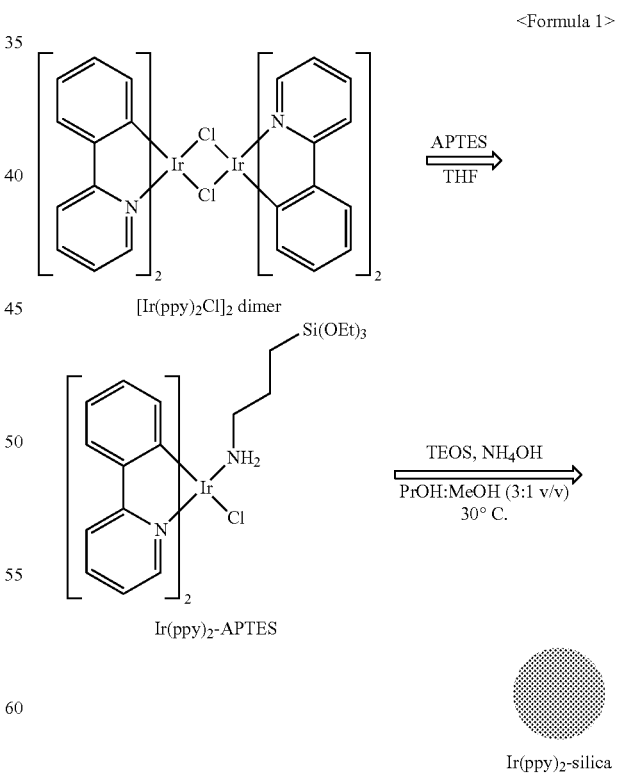

<Formula 1>

For phosphorence-emitting multilayered shell structure, the positively charged polyelectrolyte, for example, Ir(piq)$_2$-PEI complex depicted in below Formula 2 may be used.

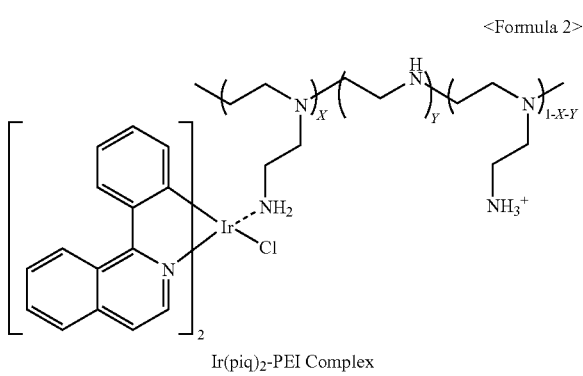

Ir(piq)₂-PEI Complex

<Formula 2>

The complex in Formula 2 includes an iridium complex, Ir(piq)₂, grafted to poly(ethylene imine) (PEI). The complex may be prepared by the ligand exchange reaction between poly(ethylene imine) (PEI) and cyclometalated iridium complex having 1-phenylisoquinoline (piq) ligand.

Cu(II) ions may be chelated to the amine groups of Ir(piq)₂-PEI complex. Accordingly, the red luminescence of Ir(III)-complex may be quenched and the luminescence intensity may gradually decrease with increasing in the concentration of Cu(II) ions. The multilayered shell may be formed by alternately depositing the positively charged Ir(piq)₂-PEI complex and the negatively charged polyelectrolyte.

The negatively charged polyelectrolyte may be, for example, a poly(acrylic acid). As illustrated in Formula 3, poly(acrylic acid) grafted with the host material such as carbazole groups (CBZ-PAA) is utilized as the negatively charged polyelectrolyte. Carbazole group is a well-known host material for the Ir(III)-complex by its high energy level. Both luminescence intensities of the red luminescent Ir(piq)₂-PEI complex in the shell region and the green luminescent Ir(ppy)₂-silica nanoparticle may be enhanced by the effective energy transfer from CBZ-PAA to a phosphorescent emitting materials. Using the host materials, the luminescence intensity of chemosensors may be enhanced, so that detection sensitivity of the sensors based on emitting characteristics may be enhanced. In one embodiment, the host material may be carbazole group. In another embodiment, the host material may be CBP (4,4'-N,N'-dicarbazole-biphenyl) having a high energy level.

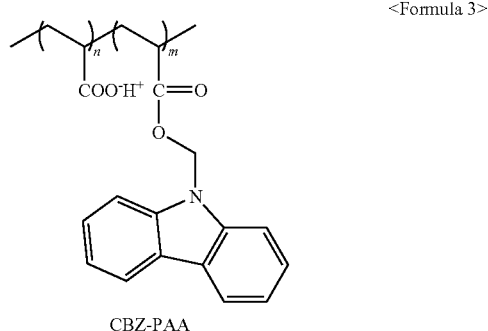

CBZ-PAA

<Formula 3>

In case that the metal ion sensor has a core/shell shape, the luminescence from the first luminescent material of the core may be protected from the exterior environment while the luminescence from the second luminescent material located at the shell may be quenched by metal ions. Thus, when the concentration of metal ions increases, the luminescence from the first luminescent material gets no effect except for the partial quenching of the first luminescent material near the surface of the core whereas the luminescence from the second luminescent material may remarkably decrease in the intensity by the quenching process. In short, the luminescence color combined by the luminescence from the core and the luminescence from the shell may rely on the variation of the luminescence intensity from the shell. The emission color of metal ion sensor containing a green luminescent core and a red luminescent shell shows reddish-orange without the presence of Cu(II) ions, and as the Cu(II) concentration is increased, the emission color is changed to orange, to yellow, and to green by the change in the relative intensity ratio between green and red emissions as a function of Cu(II) concentration. With the above properties, when the metal ion sensor is exposed to metal ions, the concentration of metal ions may be readily measured by comparing a colorimetric chart and the luminescence color under a UV lamp.

In case that the polyelectrolyte shell having a luminescent material is provided with functional groups suitable to chelate ambient metal ions, the metal ion sensor may detect other kinds of metal ions besides copper ions.

For example, the polyelectrolyte having the following luminescent materials may be utilized in the metal ion sensor: for mercury ion, (1-amino-8-naphthol-3,6-disulfonic acid sodium, ANDS); for lead ion, (dansyl chloride) derivative; for zinc ion, (6-methoxy-8-(p-toluenesulfonamido)-quinoline) derivatives; and for cadmium ion, (a,b,c,d-tetrakis(1-methylpyridinium-4-yl)porphine p-toluenesulfonate, TMPyP), (diphenylcarbazide, DPC), (4-n-dodecyl-6-(2-thiazolylazo) resorcinol, DTAR), (4-n-dodecyl-6-(2-pyridylazo)phenol, DPAP).

Each metal ion has its unique critical concentration ranges for living organism due to its toxicity, thus the detectable dynamic concentration range of the metal ion sensor should be modulated. The detection concentration range of the core/shell structured metal ion sensor may be modulated by changing the layer number of the multilayered shell. The detection concentration range may also be modulated by changing the ratio of the luminescent material presented in the multilayered shell and the luminescent material presented in the nanoparticle core. According to the kinds of metal ions, polyelectrolytes having various types of binding sites for selective binding with the corresponding metal ion may be chosen.

After detecting metal ions, the metal ion sensor may be recycled by removing adsorbed metal ions with acidic water. The original luminescence intensity may be almost completely recovered by washing with acidic water. The above ion sensor may be operated in aqueous solution without using any organic solvent and be practically applied to detect metal ions by using the rapid response speed less than 10 seconds.

In one embodiment, the metal ion sensor may be used in suspension state. In another embodiment, a metal ion sensor may be used in solid state. A solid-state metal ion sensor may be provided by applying the aforesaid metal ion sensor to a substrate. The aforesaid metal ion sensor may be attached onto various solid-type substrates, i.e. papers, glasses, plastics, metals etc., and thus portability and measuring facilitation of the metal ion sensor may be enhanced.

A method of fabricating a metal ion sensor may include: forming a nanoparticle core doped with a first luminescent material; providing a first polyelectrolyte, which is doped with a second luminescent material and has binding sites of outer metal ions; providing a second polyelectrolyte, which has an opposite electric charge to that of the first polyelectrolyte; and forming a multilayered shell by alternately depositing the first polyelectrolyte and the second polyelectrolyte on the nanoparticle core. When outer metal ions are bound to the above binding sites, the luminescence intensity in the shell region may be reduced due to the quenching mechanism.

The layer-by-layer deposition of the multilayered shell may be, for example, performed by using the following method. First, nanoparticles positively charged on the surface thereof are dispersed in a solution of a negatively charged polyelectrolytes so that the polyelectrolytes are adsorbed onto the surface of the nanoparticles. Next, the nanoparticles are centrifuged and the remained polyelectrolyte solution is removed. A washing process is executed to remove the weakly bound polyelectrolytes on the nanoparticles by adding water and redispersing of the nanoparticles. A positively charged polyelectrolyte solution is added for the adsorption on the surface of the nanoparticles having the negatively charged polyelectrolyte layer. After a washing process is executed, one bilayer structure is formed on the nanoparticle. The multilayered shell structure is formed by repeating the above processes.

FIG. 2 is a schematical view depicting one embodiment of a process of forming a multilayered shell of a metal ion sensor using a layer-by-layer deposition method. Referring to FIG. 2, the multilayered shell may be coated on the silica nanoparticle core by repeating alternate deposition of a negatively charged CBZ-PAA polyelectrolyte layer and a positively charged Ir(piq)$_2$-PEI polyelectrolyte layer onto the positively charged silica nanoparticle core.

Hereinafter, the disclosed technology will be described in more detail with the following embodiments, however, the concept of the technology is not limited to the described embodiments.

Synthesis of Silica Nanoparticle Core Embedded with Ir(III)-Complex

For the nanoparticle synthesis, solutions and reaction materials were purchased from Aldrich and Samjeon Chemical and used without purification. IrCl$_3$.nH$_2$O and 2-phenylpyridine (ppy) were used from the products of Aldrich. Ir(III)-dichloro-bridged dimer, [Ir(ppy)$_2$Cl]$_2$ was synthesized via the Nonoyama route by refluxing IrCl$_3$.nH$_2$O with 2-2.5 equiv. of cyclometalated ligands, ppy, in a 3:1 mixture of 2-ethoxyethanol and water. [Ir(ppy)$_2$Cl]$_2$ dimer was dissolved in 5 ml of tetrahydrofuran (THF) and mixed with an excess of (3-aminopropyl)triethoxysilane (APTES) at a molar ratio of [Ir(ppy)$_2$Cl]$_2$ dimer to APTES of 1:2.5 and stirred for 12 hours at room temperature in an inert gas condition to prepare the Ir(ppy)$_2$-APTES complex. For the synthesis of Ir(III)-silica nanoparticle, Stöber method was adopted. 1 ml of tetraethoxysilane (TEOS) was added to a 3:1 mixture of 1-propanol and methanol with 2.8 ml of ammonium hydroxide solution at 30° C. After 4 minutes, the Ir(ppy)$_2$-APTES complex was added to the above mixture and stirred for 2 hours in a dark condition. After completion of the reaction, the sample was centrifuged at 10,000 rpm for 10 minutes to collect Ir(ppy)$_2$-doped silica nanoparticle and then washed with THF and methanol to remove unreacted chemicals.

FIG. 3 shows (a) an field emission scanning electron microscope (FE-SEM) image of prepared Ir(ppy)$_2$-silica nanoparticles and (b) luminescence spectrum of the Ir(ppy)$_2$-silica nanoparticles. As shown in FIG. 3(a), when observed by FE-SEM (JEOL JSM7401F), the Ir(ppy)$_2$-silica nanoparticles have an average diameter of 211 nm with 4.3% polydispersity. As shown in FIG. 3(b), the Ir(ppy)$_2$-silica nanoparticles have strong phosphorescent emission peaks at 488 nm and 511 nm. The surface of the Ir(ppy)$_2$-silica nanoparticle is positively charged by an excess of APTES.

Fabrication of Multilayered Shell Structure on Ir(III)-Complex Embedded Silica Nanoparticle Core 1. Synthesis of Ir(piq)$_2$-PEI A positively charged polyelectrolyte, Ir(piq)$_2$-PEI, containing a phosphorescent material was synthesized as follows for the layer-by-layer deposition in the shell region. Ir(III)-dichloro-bridged dimer, [Ir(piq)$_2$Cl]$_2$ was synthesized via the Nonoyama route by refluxing IrCl$_3$.nH$_2$O with 2-2.5 equiv. of cyclometalated ligands, 1-phenylisoquinoline (piq), in a 3:1 mixture of 2-ethoxyethanol and water. Ir(piq)$_2$-PEI complex was synthesized by reacting [Ir(piq)$_2$Cl]$_2$ and PEI in chloroform solution and then purifying the same.

2. Synthesis of CBZ-PAA

As a negatively charged polyelectrolyte is required for the layer-by-layer deposition in the shell region, poly(acrylic acid) grafted with carbazole groups (CBZ-PAA) was synthesized as follows. 15 mol of CDI (N,N'-carbonyldiimidazole) and a catalytic amount of DBU (1,8-diazabicyclo [5,4,0] undec-7-ene) were added to 30 mol of poly(acrylic acid), and 15 mol of carbazole ethanol (9H-carbazole-9-ethanol) was mixed for the esterification reaction between carboxylic acid group and hydroxyl group, thus poly(acrylic acid) partially substituted by carbazole group, CBZ-PAA was synthesized.

3. Layer-by-Layer Deposition

A polyelectrolyte multilayered shell was deposited on the Ir(ppy)$_2$-silica nanoparticle by using a layer-by-layer deposition method. Positively charged Ir-silica nanoparticles were dispersed in deionized water with 2 wt % concentrations. 1.0 mL of negatively charged CBZ-PAA solution was added to Ir-silica nanoparticles. After deposition for 15 min, the excess polyelectrolytes were removed by centrifugation and then washed with deionized water for the removal of weakly bound CBZ-PAA polyelectrolytes on the Ir-silica nanoparticles. Positively charged Ir(piq)$_2$-PEI complexes were then deposited onto the negatively charged silica cores due to adsorption of CBZ-PAA under the same conditions. The above processes were repeated until desired number of bilayers was obtained. Ultrapure water (<18 MΩcm) was used in all embodiments of the present disclosure and the pH of deposition solution was adjusted by 1 M of HCl or NaOH.

4. Characteristic Evaluation

Figure 4:
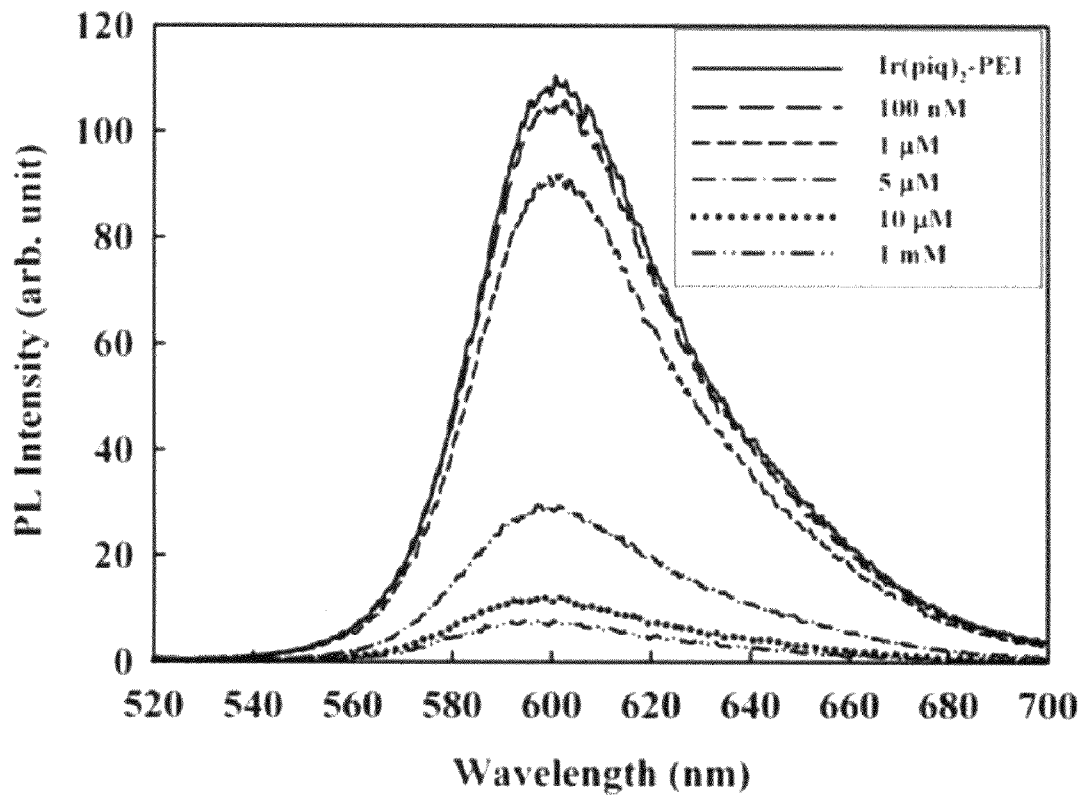
FIG. 4 shows quenching behavior of the luminescence intensity of $Ir(piq)_2$-PEI solution depicted as a function of Cu(II) concentration.

FIG. 4 shows quenching behavior of the luminescence intensity of Ir(piq)$_2$-PEI solution depicted as a function of Cu(II) concentration. PEI may act as a metal chelating agent for Cu(II) ions. As shown in FIG. 4, the red luminescence intensity of the Ir(piq)$_2$-PEI complex in aqueous solution gradually decreases according to the increase of the Cu(II) ion concentration due to the paramagnetic quenching property thereof.

Figure 5:
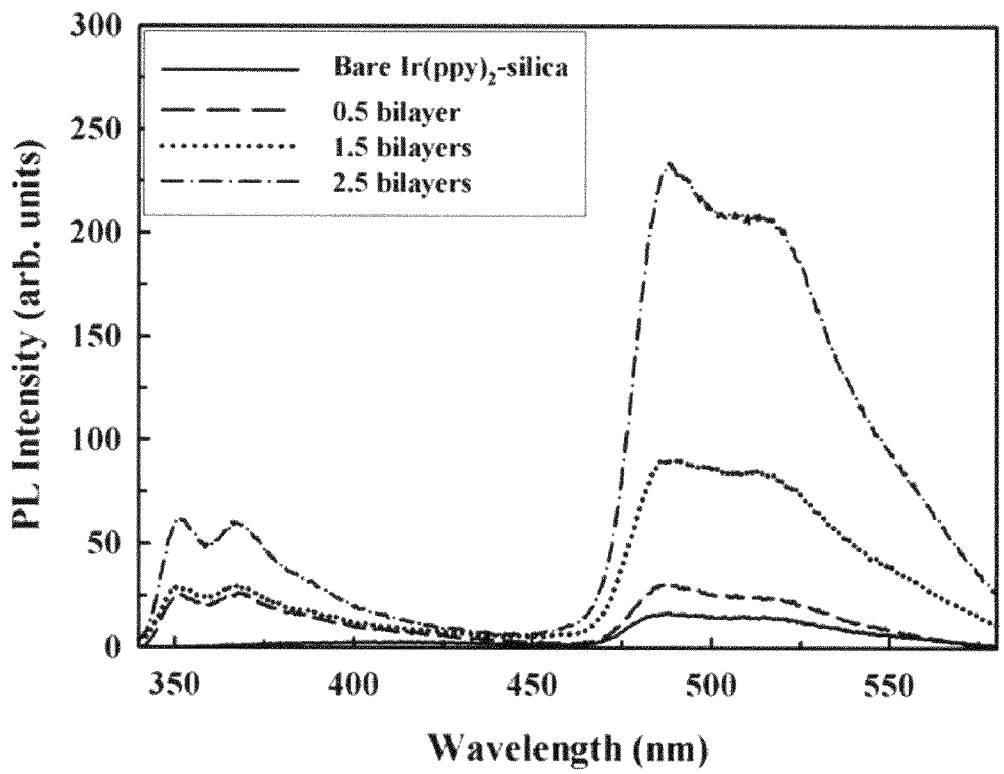
FIG. 5 shows luminescence spectra of $Ir(ppy)_2$-silica/$(CBZ-PAA/PAH)_n$.

FIG. 5 shows luminescence spectra of Ir(ppy)$_2$-silica/ (CBZ-PAA/PAH)$_n$. The "n" denotes the number of the bilayers. Referring to FIG. 5, the luminescence intensity of the Ir(ppy)$_2$-silica particle with a bilayer shell of CBZ-PAA and PAH (poly(allylamine) hydrochloride) increases compared to the luminescence intensity of the Ir(ppy)$_2$-silica particle without any shell. When the number (n) of the bilayers increases, the luminescence intensity of Ir(ppy)$_2$-silica is improved by the energy transfer from CBZ-PAA to Ir(ppy)$_2$ dyes embedded in silica. The luminescence peak near 350 nm comes from carbazole groups of CBZ-PAA.

Figure 6:
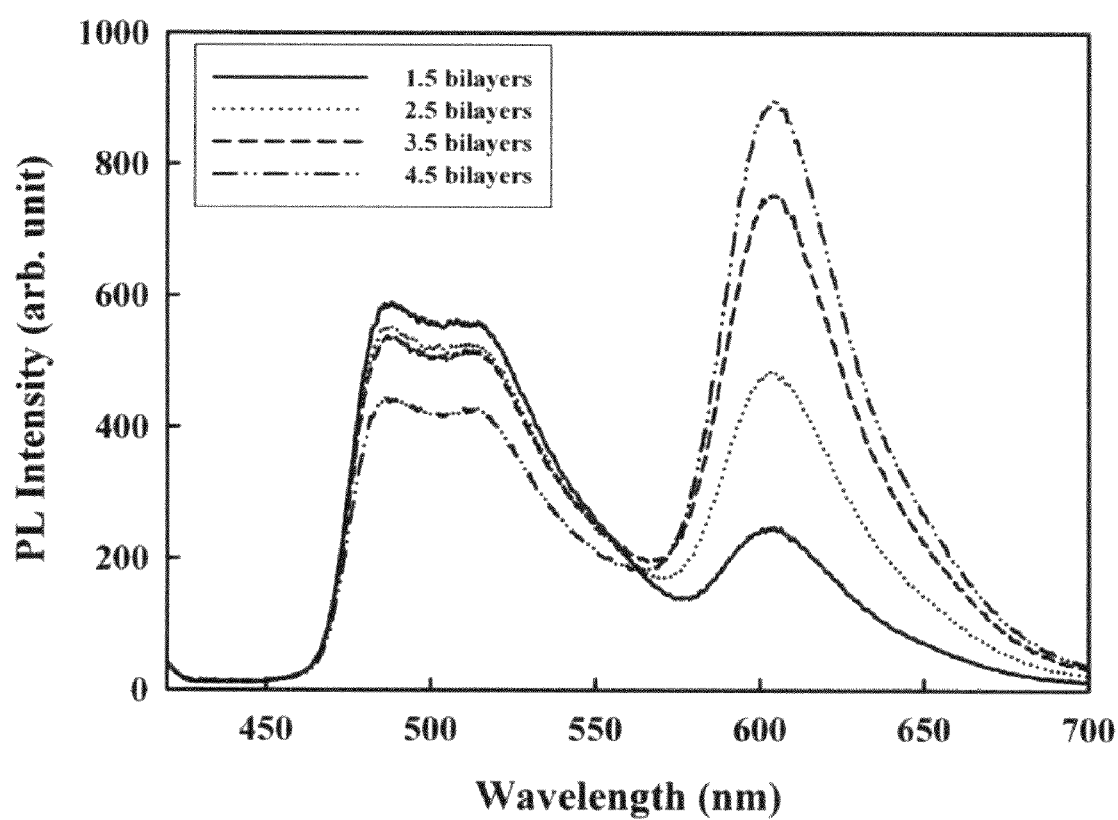
FIG. 6 shows luminescence spectra of $Ir(ppy)_2$-silica/$(CBZ-PAA/Ir(piq)_2-PEI)_n$.

FIG. 6 shows luminescence spectra of Ir(ppy)$_2$-silica/ (CBZ-PAA/Ir(piq)$_2$-PEI)$_n$. The CBZ-PAA/Ir(piq)$_2$-PEI multilayered shell may be prepared by using the layer-by-layer deposition. Referring to FIG. 6, the growth of the multilayered shell may be observed by the increase of the red luminescence intensity from the Ir(piq)$_2$-PEI complex according to the increase of the deposition number of the bilayers. The prepared core/shell structured nanoparticle emits red-orange luminescence by the partial energy transfer from green to red dyes, placed in the regions of the core and the shell, respectively.

Figure 7:
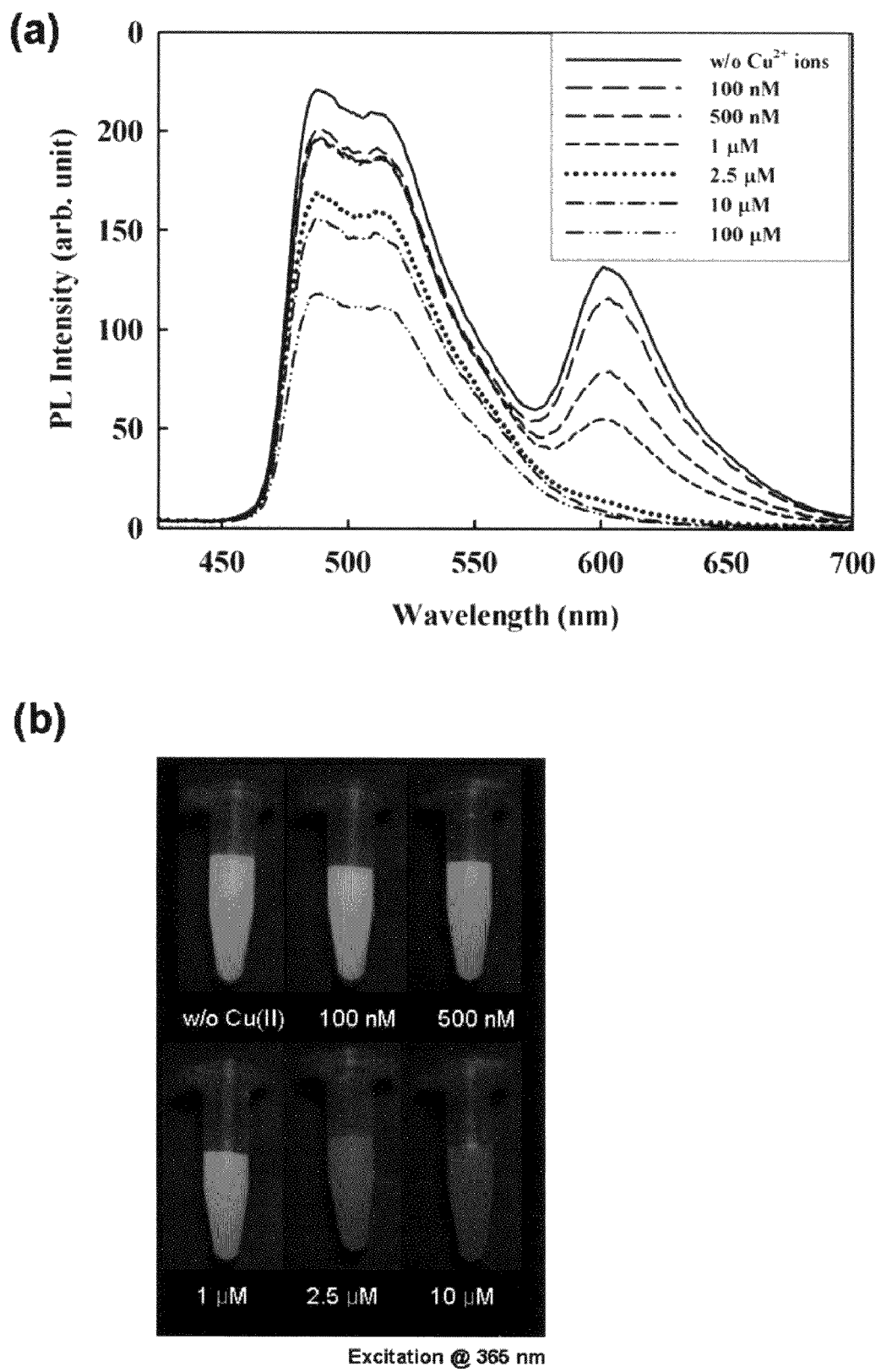
FIG. 7 shows (a) luminescence spectra of a copper ion sensor having a $Ir(ppy)_2$-silica/$(CBZ-PAA/Ir(piq)_2-PEI)_{2.5}$ core/shell structure with various Cu(II) ion concentrations and (b) photographs for depicting luminescence of the copper ion sensor in the form of suspension added with solutions having different concentrations of Cu(II) ions.

FIG. 7 shows (a) luminescence spectra of a copper ion sensor having a Ir(ppy)$_2$-silica/(CBZ-PAA/Ir(piq)$_2$-PEI)$_{2.5}$ core/shell structure with various Cu(II) ion concentrations and (b) photographs for depicting luminescence of the copper ion sensor in the form of suspension added with solutions having different concentrations of Cu(II) ions.

Referring to FIG. 7(a), luminescence spectra are measured at the excitation wavelength of 365 nm for suspensions containing 0.1 ml of 0.5 wt % core/shell-structured silica mixed with different concentrations of 3 ml CuCl$_2$ aqueous solution. As the Cu(II) ion concentration increases, both luminescence intensities from the Ir(piq)$_2$-PEI complex as well as the Ir(ppy)$_2$-silica are gradually reduced, but red luminescence from the Ir(piq)$_2$-PEI complex in the shell region is more rapidly decayed than green luminescence from the Ir(ppy)$_2$-silica. The red luminescence is completely quenched in about 10 µM Cu(II) ion solution while the green luminescence intensity presented in the silica nanoparticle still remains even in 100 µM Cu(II) solution.

Referring to FIG. 7(b), under UV irradiation of 365 nm, the luminescence of the nanoparticle without the presence of Cu(II) ions shows reddish-orange. As the Cu(II) ion concentration increases, the luminescence color is consecutively changed to orange, yellow and then green by the relative intensity variation of green luminescence and red luminescence. The colorimetric and ratiometric properties of such Cu(II) ion sensors enable the simple quantitative analysis of Cu(II) ions without using any costly instruments. As a result, the Cu(II) concentration may be taken by comparing the colorimetric chart and the luminescence color under a UV lamp.

Dynamic Concentration Range of Copper Ion Sensor with Variation of Shell Thickness The dynamic concentration range of core/shell-structured Cu(II) ion sensors may be modulated by varying the bilayer number of the multilayered shells.

FIG. 8 shows (a) a graph showing a ratio (I/I$_0$) of the luminescence intensity (I) at 602 nm with the presence of Cu(II) ions to the luminescence intensity (I$_0$) at 602 nm without Cu(II) ions for a copper sensor having a Ir(ppy)$_2$-silica/ (CBZ-PAA/Ir(piq)$_2$-PEI)$_n$ core/shell structure and (b) photographs for depicting luminescence of a copper ion sensor having a Ir(ppy)$_2$-silica/(CBZ-PAA/Ir(piq)$_2$-PEI)$_{4.5}$ core/shell structure under UV irradiation of 365 nm with various Cu(II) ion concentrations.

As shown in FIG. 8(a), the variation of the luminescence color occurs Cu(II) ion concentration from 100 nM to 3 µM for 2.5 bilayers and from 3 µM to 10 µM for 4.5 bilayers of shell layers. As illustrated in FIG. 8(b), when the multilayered shell has 4.5 bilayers, a noticeable change in luminescence color is hardly observed with the Cu(II) ion concentration below 2 µM but the luminescence color shows a remarkable change with the Cu(II) ion concentration ranging between 3 µM and 10 µM. Consequently, the adsorbed amount of Ir (piq)$_2$-PEI complexes in multilayered shells may determine the concentration detection range of Cu(II) ions, thus Cu(II) ion sensors having proper detection concentration ranges for specific applications may be prepared.

Metal Selectivity of Copper Ion Sensor

Figure 9:
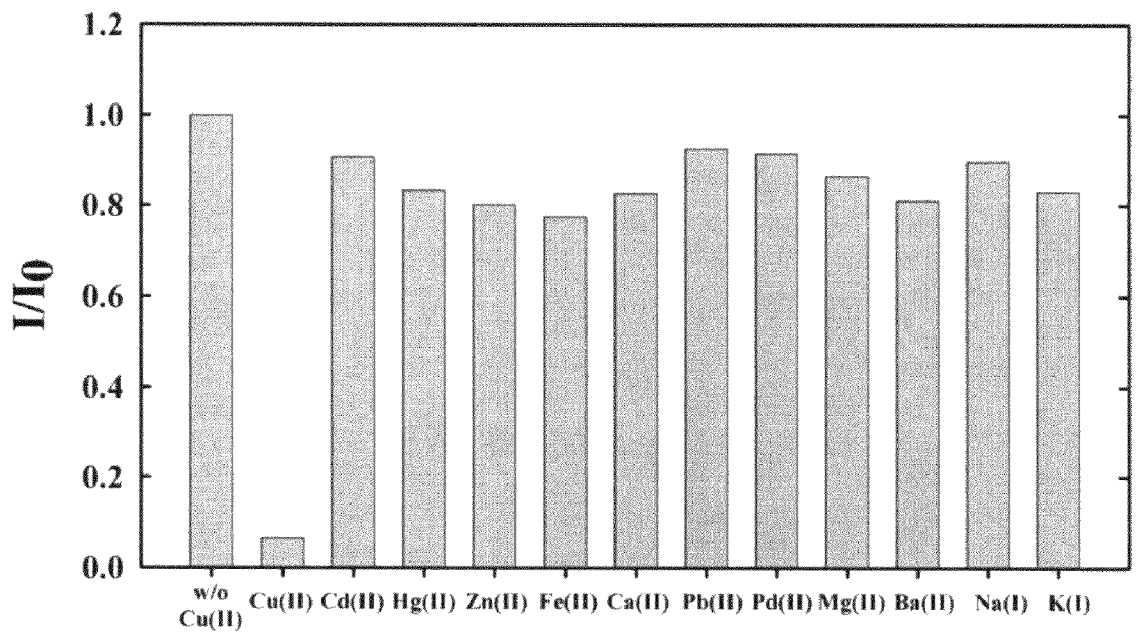
FIG. 9 is a graph showing a ratio $(I/I_0)$ of the luminescence intensity (I) at 602 nm with the presence of 10 μM metal ions to the luminescence intensity $(I_0)$ at 602 nm without metal ions for a copper ion sensor having a $Ir(ppy)_2$-silica/$(CBZ-PAA/Ir(piq)_2-PEI)_{2.5}$ core/shell with the presence of various metal ions.

FIG. 9 is a graph showing a ratio (I/I$_0$) of the luminescence intensity (I) at 602 nm with the presence of 10 µM metal ions to the luminescence intensity (I$_0$) at 602 nm without metal ions for a copper ion sensor having a Ir(ppy)$_2$-silica/(CBZ-PAA/Ir(piq)$_2$-PEI)$_{2.5}$ core/shell with the presence of various metal ions. As illustrated in FIG. 9, for 10 µM Cu(II) solution, 93% quenching of the phosphorescent intensity is observed. On the other hand, Cd(II), Pb(II), Pd(II), Mg(II), and Na(I) ions show the quenching less than 15% while other metal ions such as Hg(II), Zn(II), Fe(II), Ca(II), Ba(II), and K(I) show phosphorescent quenching of around 20%. The above result implies that no significant changes in luminescence color are observed with metal ions, except Cu(II) ions, and demonstrates high selectivity for Cu(II) ions.

Recyclability of Copper Ion Sensor

The Cu(II) metal ion sensors acquire recyclability or reusability by simply washing off adsorbed Cu(II) ions with acidic (pH ~2) water.

Figure 10:
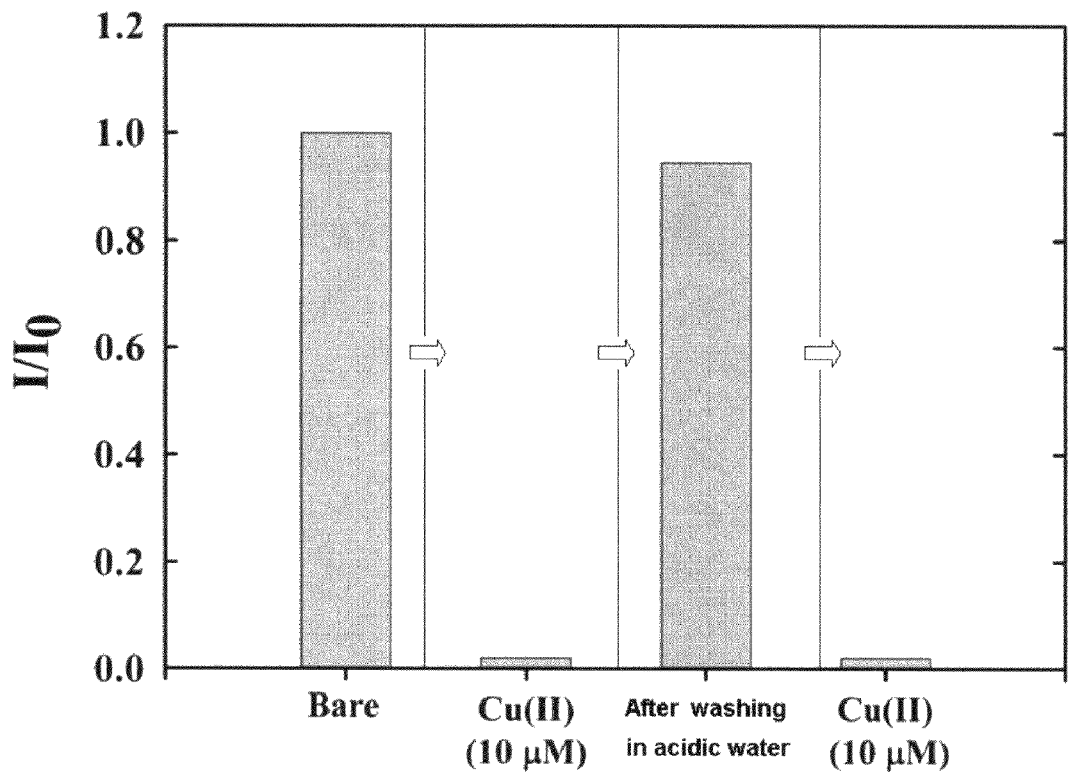
FIG. 10 is a graph showing a variation of the luminescence intensity ratio $(I/I_0)$ after washing a Cu(II)-adsorbed sensor treated with 10 μM of $CuCl_2$ solution with acidic water.

FIG. 10 is a graph showing a variation of the luminescence intensity ratio (I/I$_0$) after washing a Cu(II)-adsorbed sensor treated with 10 µM of CuCl$_2$ solution with acidic water. Referring to FIG. 10, the luminescence intensity at 602 nm may be recovered up to 96% of the original luminescence intensity when acidic water is added to Cu(II)-adsorbed sensors upon treatment with 10 µM CuCl$_2$ solution.

Fabrication of Solid-State Copper Ion Sensor

Copper ion sensors in suspension state were prepared firstly. The copper ion sensors have 2.5 or 4.5 CBZ-PAA/Ir (piq)$_2$-PEI bilayer shell on the green luminescent Ir(ppy)$_2$-silica nanoparticle core. The copper ion sensors were dispersed in water to form suspension state. A predetermined amount of the suspension was loaded and dried on a filter paper to obtain a solid-state copper ion sensor. The solid-state copper ion sensor was immersed for a predetermined period of time (~30 seconds) in aqueous solution containing copper ions. After the immersion, the solid-state copper ion sensor was taken out from the aqueous solution to observe the change of the luminescence colors under a UV lamp.

Figure 11:
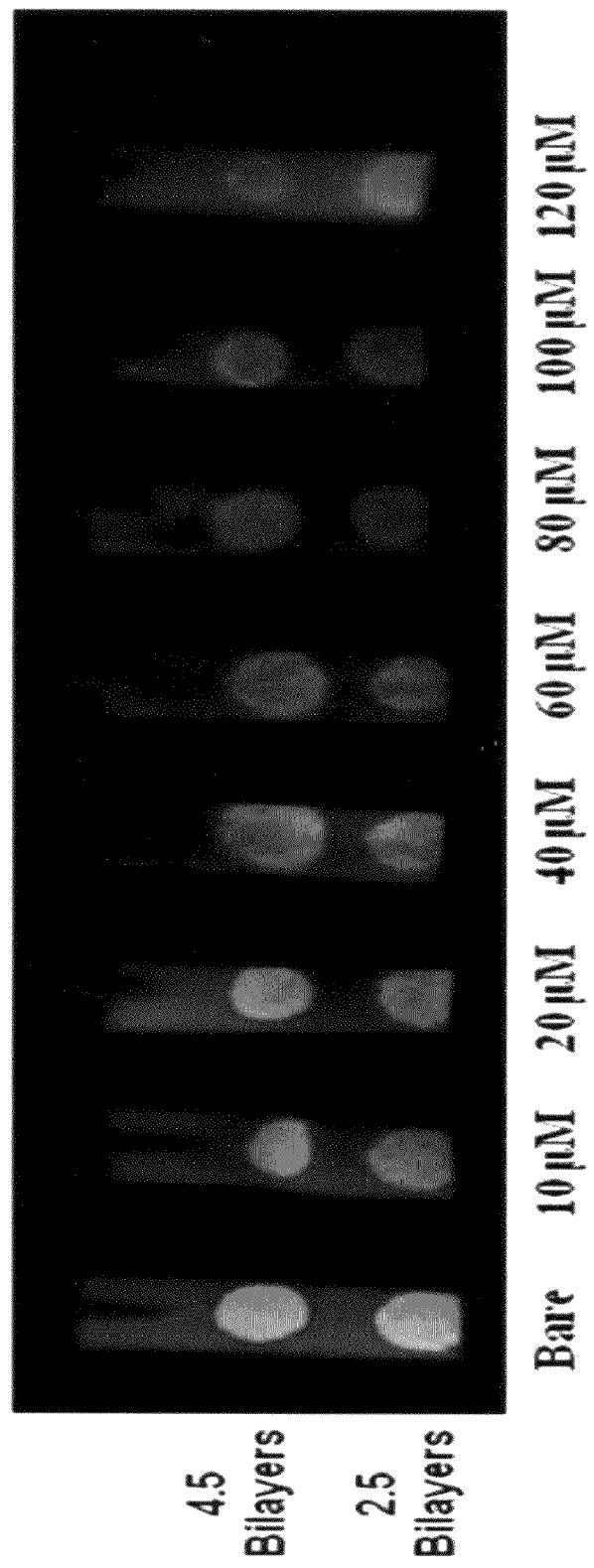
FIG. 11 is a photograph showing a solid-state metal ion sensor treated with various Cu(II) ion concentrations.

FIG. 11 is a photograph showing a solid-state copper ion sensor treated with various Cu(II) ion concentrations. Referring to FIG. 11, luminescence color of core/shell particles is changed from orange to green corresponding to the copper ion concentration. The detection range of copper ion concentration is approximately from 10 µM to 60 µM in the 2.5 bilayers. When the core/shell particles have 4.5 bilayers, the luminescence color changes with the copper ion concentration from 60 µM to 120 µM. This represents that the aforementioned variation of the detection concentration range corresponding to the deposition number may be applied even in the solid-state copper ion sensor.

As apparent from the foregoing, a novel Cu(II) ion sensor is provided based on the selective phosphorescent quenching of a red luminescent Ir(piq)$_2$-PEI polyelectrolyte deposited on a green luminescent Ir(ppy)$_2$-silica nanoparticle by a layer-by-layer deposition. The core/shell structured sensor shows the changing of the luminescence color from reddish-orange to green as a function of the Cu(II) concentration and enables a facile quantitative analysis of Cu(II) ions by simply examining the luminescence color with calibrated color chart. The dynamic concentration range of the Cu(II) ion sensor may be modulated by increasing the adsorbed amount of Ir(piq)$_2$-PEI complexes in the multilayered shell deposited on the silica nanoparticle. In addition, the Cu(II) ion sensor may be activated in pure aqueous solution with high copper selectivity, reversibility (reusability), and relatively fast response speed. Other metal ion sensors may also be used through judicious selection of phosphorescent (or fluorescent) dyes and metal ion receptors. Moreover, various types of nanotemplates besides the bead shape are readily functionalized with metal-detecting materials by using the layer-by-layer deposition technique.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A metal ion sensor, comprising:
   a nanoparticle core doped with a first luminescent material; and
   a shell enclosing the nanoparticle core,
   wherein the shell includes a second luminescent material and binding sites of outer metal ions,
   wherein the first luminescent material and the second luminescent material emit light with mutually different colors when excited by an excitation source, and
   wherein the luminescence intensity of the light emitted from the second luminescent material varies in accordance with the binding amount of the outer metal ions, such that the emission color of the combined luminescence of the first luminescent material and the second luminescent material is variable.

2. The metal ion sensor of claim 1, wherein the shell includes a multilayered shell.

3. The metal ion sensor of claim 1, wherein the shell includes polymeric bilayers.

4. The metal ion sensor of claim 3, wherein the polymeric bilayer is formed by at least one of noncovalent interaction and covalent bonding between each polymer layer composing the polymeric bilayer.

5. The metal ion sensor of claim 3, wherein a detection concentration range of the outer metal ions is modulated by changing the bilayer number in the multilayered shell.

6. The metal ion sensor of claim 1, wherein the shell includes an alternate stacking structure of a first polyelectrolyte layer and a second polyelectrolyte layer, the first polyelectrolyte layer and the second polyelectrolyte layer having electric charges opposite to each other.

7. The metal ion sensor of claim 6, wherein at least one of the first polyelectrolyte and the second polyelectrolyte is grafted with a host material to improve the luminescence intensity of the at least one of the first luminescent material and the second luminescent material.

8. The metal ion sensor of claim 1, wherein the nanoparticle core is selected from at least one of silica beads, quantum dots, inorganic nanoparticles, and polymer beads.

9. The metal ion sensor of claim 1, wherein the first luminescent material is selected from at least one of dyes, pigments, and semiconductor nanoparticles.

10. The metal ion sensor of claim 1, wherein the second luminescent material is selected from at least one of dyes, pigments, and semiconductor nanoparticles.

11. The metal ion sensor of claim 1, wherein the binding sites include at least one of nonionic functional groups and negatively charged functional groups.

12. A solid-state metal ion sensor fabricated by applying a metal ion sensor to a substrate, the metal ion sensor comprising:
   a nanoparticle core doped with a first luminescent material; and
   a multilayered shell enclosing the nanoparticle core;
   wherein the multilayered shell includes a second luminescent material and binding sites of outer metal ions;
   wherein the first luminescent material and the second luminescent material emit light with mutually different colors when excited by an excitation source; and
   wherein the luminescence intensity of the light emitted from the second luminescent material varies in accordance with the binding amount of the outer metal ions, such that the emission color of the combined luminescence of the first luminescent material and the second luminescent material is variable.

13. The solid-state metal ion sensor of claim 12, wherein the multilayered shell includes polymeric bilayers.

14. The solid-state metal ion sensor of claim 12, wherein the multilayered shell includes an alternate stacking structure of a first polyelectrolyte layer and a second polyelectrolyte layer, the first polyelectrolyte layer and the second polyelectrolyte layer having electric charges opposite to each other.

15. A copper ion sensor, comprising:
   a nanoparticle core doped with a first luminescent material; and
   a multilayered shell enclosing the nanoparticle core and being doped with a second luminescent material, the second luminescent material having a different luminescence color from that of the first luminescent material;
   wherein the multilayered shell has an alternate stacking structure of a negatively charged polyelectrolyte layer and a positively charged polyelectrolyte layer and has binding sites of outer copper ions; and
   wherein the luminescence from the multilayered shell is selectively quenched by the binding of copper ions when the first luminescent material and the second luminescent material are excited by an excitation source.

16. The copper ion sensor of claim 15, wherein the nanoparticle core is selected from at least one of silica beads, quantum dots, inorganic nanoparticles, and polymer beads.

17. The copper ion sensor of claim 15, wherein the positively charged polyelectrolyte layer includes a polyelectrolyte in which the second luminescent material is grafted onto polyethylene imine (PEI).

18. The copper ion sensor of claim 15, wherein the negatively charged polyelectrolyte layer includes poly(acrylic acid) grafted with CBZ (carbazole) or CBP (4,4'-N,N'-dicarbazole-biphenyl).

19. The copper ion sensor of claim 15, wherein a detection concentration range of the outer copper ions is modulated by changing the bilayer number in the multilayered shell.

* * * * *